(12) United States Patent
Ota et al.

(10) Patent No.: US 10,029,064 B2
(45) Date of Patent: Jul. 24, 2018

(54) SOUND MUFFLER AND OXYGEN CONCENTRATION DEVICE COMPRISING THE SAME

(71) Applicant: Teijin Pharma Limited, Tokyo (JP)

(72) Inventors: Shoko Ota, Yamaguchi (JP); Katsunori Kuwabara, Yamaguchi (JP)

(73) Assignee: TEIJIN PHARMA LIMITED, Tokyo (JP)

(*) Notice: Subject to any disclaimer, the term of this patent is extended or adjusted under 35 U.S.C. 154(b) by 593 days.

(21) Appl. No.: 14/388,564

(22) PCT Filed: Mar. 25, 2013

(86) PCT No.: PCT/JP2013/059787
§ 371 (c)(1),
(2) Date: Sep. 26, 2014

(87) PCT Pub. No.: WO2013/147283
PCT Pub. Date: Oct. 3, 2013

(65) Prior Publication Data
US 2015/0059741 A1    Mar. 5, 2015

(30) Foreign Application Priority Data

Mar. 27, 2012 (JP) .................................. 2012-071624

(51) Int. Cl.
*A61M 16/10* (2006.01)
*A61M 16/16* (2006.01)
(Continued)

(52) U.S. Cl.
CPC ...... *A61M 16/101* (2014.02); *A61M 16/0003* (2014.02); *A61M 16/0875* (2013.01);
(Continued)

(58) Field of Classification Search
CPC ............ A61M 16/101; A61M 16/0003; A61M 16/0875; A61M 16/10; A61M 16/105; A61M 16/16; A61M 16/208
See application file for complete search history.

(56) References Cited

U.S. PATENT DOCUMENTS

| 4,789,388 A | * | 12/1988 | Nishibata | ............... B01D 53/22 96/381 |
| 6,881,237 B2 | | 4/2005 | Storz et al. | |

(Continued)

FOREIGN PATENT DOCUMENTS

| JP | H06-058131 A | 3/1994 |
| JP | H10-25203 A | 9/1998 |

(Continued)

OTHER PUBLICATIONS

Office Action issued in Japanese Application No. 2014-508249, dated Aug. 4, 2015.
(Continued)

*Primary Examiner* — (Jackie) Tan-Uyen T Ho
*Assistant Examiner* — Jonathan Paciorek
(74) *Attorney, Agent, or Firm* — Michael Best & Friedrich LLP (57) ABSTRACT

Provided is an expansion-chamber muffler as a downsized sound muffler while keeping a function of noise reduction, comprising:
a tube (A) which supplies and evacuates a gas having a noise, wherein the tube (A) in the midway has a cavity with a cross-sectional area larger than that of the tube (A); and
at least two or more ports for inflow or outflow of the gas on the lateral side of a tube (B) extending from the expansion-chamber muffler, on the opposite side of the noise source generating the noise.

19 Claims, 6 Drawing Sheets

(51) Int. Cl.
  *A61M 16/20* (2006.01)
  *A61M 16/00* (2006.01)
  *A61M 16/08* (2006.01)
  *C01B 13/02* (2006.01)
  *B01D 53/047* (2006.01)
  *A61M 16/14* (2006.01)

(52) U.S. Cl.
  CPC .......... *A61M 16/10* (2013.01); *A61M 16/105* (2013.01); *A61M 16/16* (2013.01); *A61M 16/208* (2013.01); *B01D 53/047* (2013.01); *C01B 13/0259* (2013.01); *A61M 16/107* (2014.02); *A61M 16/145* (2014.02); *A61M 2016/003* (2013.01); *A61M 2016/1025* (2013.01); *A61M 2202/0208* (2013.01); *A61M 2202/0266* (2013.01); *A61M 2205/3334* (2013.01); *A61M 2205/42* (2013.01); *A61M 2205/75* (2013.01); *B01D 2256/12* (2013.01); *B01D 2257/102* (2013.01); *B01D 2259/402* (2013.01); *B01D 2259/4533* (2013.01)

(56) References Cited

U.S. PATENT DOCUMENTS

| | | | |
|---|---|---|---|
| 6,892,853 B2 * | 5/2005 | Cai | F01N 1/087 181/249 |
| 7,582,143 B2 * | 9/2009 | Berger | B01D 45/08 95/52 |
| 7,878,300 B2 * | 2/2011 | Sammut | F01N 1/006 181/238 |
| 2004/0060445 A1 * | 4/2004 | Fujimoto | B01D 53/0454 96/110 |
| 2009/0188217 A1 | 7/2009 | Amann | |
| 2010/0242734 A1 * | 9/2010 | Maeda | A61M 16/10 96/110 |

FOREIGN PATENT DOCUMENTS

| | | |
|---|---|---|
| JP | 2003-235982 A | 8/2003 |
| JP | 2003-328884 A | 11/2003 |
| JP | 2005-006731 A | 1/2005 |
| JP | 2007-020601 A | 2/2007 |
| JP | 2008-212206 A | 9/2008 |
| JP | 2005-111016 A | 4/2015 |

OTHER PUBLICATIONS

International Search Report issued in Application No. PCT/JP2013/059787, dated Jul. 2, 2013.

* cited by examiner

SOUND MUFFLER AND OXYGEN CONCENTRATION DEVICE COMPRISING THE SAME

TECHNICAL FIELD

The present invention relates to a sound muffler, especially to a medical oxygen concentration device providing users such as patients having respiratory disease with oxygen-enriched air, and to a sound muffler used for reducing the particularly problematic noise during operation of the device.

BACKGROUND ART

In recent years, an increasing number of patients is suffering from respiratory diseases such as asthma, pulmonary emphysema, chronic bronchitis, etc. One of the most effective therapies for these diseases is oxygen inhalation therapy. Such oxygen inhalation therapy makes the patient inhale oxygen gas or oxygen-enriched air. An oxygen concentration device, liquid oxygen, an oxygen gas cylinder, etc. are known as the oxygen source, among which the oxygen concentration device is mainly used for home oxygen therapy due to its convenience in using and easiness in maintenance.

The oxygen concentration device concentrates oxygen present in the air at about 21% and supplies an oxygen-enriched gas. The oxygen concentration device includes a membrane-type oxygen concentration device utilizing a membrane which selectively permeates oxygen and a pressure-swing adsorption type oxygen concentration device utilizing an adsorbent which is capable of preferentially adsorb nitrogen or oxygen. The latter is mainly used because higher concentration of oxygen is obtained.

In the pressure-swing adsorption type oxygen concentration device, oxygen is generated by supplying air compressed using a compressor to an adsorbent cylinder filled with molecular sieve zeolite such as 5A type, 13X type, Li—X type, etc. as the adsorbent which preferentially adsorbs nitrogen over oxygen. Highly concentrated oxygen-enriched gas is continuously generated by alternately repeating a pressurization/adsorption step in which nitrogen is adsorbed on the adsorbent in the adsorbent cylinder under a pressurized condition and unadsorbed oxygen-enriched gas is obtained and a depressurization/desorption step in which the adsorbent is regenerated by reducing the pressure in the adsorbent cylinder to atmospheric pressure or lower and purging nitrogen adsorbed on the adsorbent.

Such an oxygen concentration device is intended to be placed relatively close to the patient and is essentially used continuously throughout the day by the patient regardless of dining or bedtime. Therefore, a noise generated from the oxygen concentration device is directly heard by the patient or patient's family, etc. and may give unpleasant feeling to them. In particular, the noise generated by the device has a significant influence on the patient or the family during sleep, and there is concern that the noise generated by the oxygen concentration device negatively affects their mental health by disturbing their sleep.

Sources of the noise generated by a pressure-swing adsorption type oxygen concentration device include a structure-borne sound from a compressor which supplies pressurized air to an adsorption cylinder and used for pressure variation, a suction sound and an exhaust sound from the compressor, an operating noise from a motor for driving the compressor, a purge gas flow noise generated when purging the adsorbent cylinder, and an operating noise from a cooling fan for cooling the interior of the oxygen concentration device housing. Among them, noises originated from the compressor such as the structure-borne sound radiation generated by the compressor itself, suction sound and exhaust sound of the compressor account for a large proportion of noises generated by the entire device.

As described above, reduction of the noise from noise sources such as the compressor is a vital issue in the oxygen concentration device. A sound muffler called a cavity type or an expansion type has been used to reduce the suction sound and the exhaust sound of the compressor, or gas flow sounds such as various purge sounds in a conventional oxygen concentration device. Furthermore, there are strong demands by patients for downsizing and weight reduction of the oxygen concentration device. As a method for satisfying both of the requests, in a sound muffler described in Japanese Patent Laid-Open Publication No. H10-245203, for example, it has been proposed that space saving can be achieved by eliminating dead space by shaping the sound muffler into a cuboid and by integrating the sound muffler into an attachment part of the air filter.

However, the expansion-chamber muffler described above has such a feature that, as the ratio of the spatial cross-sectional area of an expansion chamber to that of a tube increases, the attenuation rate of the emitted sound increases, and the length of the cavity portion of the expansion chamber is related to the frequency of the sound desired to be reduced. Therefore, the physical size of the cavity portion of the expansion chamber is determined by the frequency band and the attenuation rate of the noise desired to be reduced, which has been one of the obstacles for achieving downsizing and weight reduction of the body of a low-noise oxygen concentration device.

Thus, in order to perform downsizing and weight reduction of the device mounting a sound muffler, while increasing the sound reducing effect, Japanese Patent Laid-Open Publication No. 2003-235982, for example, discloses a technique in which a small form of the device is maintained while serving sound attenuation by bringing an expansion-chamber muffler and a resonance muffler together and placing each muffler into the dead space inside the housing of the device.

As a sound muffler for attenuating a noise in high frequency band and low frequency band based on different principles, such technique as described in Japanese Patent Laid-Open Publication No. 2005-6731 has been disclosed. In this patented technology, two sound mufflers are provided to reduce noises in high frequency band and low frequency band, where a long flow path is constituted using a sound-absorbing material for reducing the former, and this sound muffler is in turn incorporated in an expansion-chamber muffler for reducing the latter noise in the low frequency band, thereby achieving sound attenuation as well as downsizing and weight reduction. However, the expansion-chamber muffler requires the same size as before to reduce the noise in the low frequency band, and the fundamental technical problem remains unsolved.

PRIOR ART DOCUMENTS

Japanese Patent Laid-Open Publication No. H10-245203
Japanese Patent Laid-Open Publication No. 2003-235982
Japanese Patent Laid-Open Publication No. 2005-6731

SUMMARY OF INVENTION

Problems to be Solved by the Invention

Regarding a recent oxygen concentration device, demands by the users are strong for further noise reduction as well as for downsizing and weight reduction of the device for portability. To meet such demands, downsizing a sound muffler itself and improving noise reduction function have become a mandatory requirement. However, the shape of an expansion-chamber muffler is generally designed by a theoretical formula called a transmission loss as shown by the following Formula 1, thus determined by a frequency band and sound pressure level of the noise desired to be reduced. In many cases, the frequency band of the noise to be suppressed tends to be currently in the low frequency band in the oxygen concentration device and as a result, a large cavity shape has become necessary. Further, the results of a comparison of the expected sound pressure level derived from Formula 1 with the sound pressure level observed by the sound muffler that is actually designed by Formula 1 often show that the noise reduction in the low frequency band is not sufficiently achieved as predicted, and it may be necessary in some cases to enlarge the shape of the cavity portion further.

$$TL = 10 \log_{10} \frac{1}{4}\left[\left(1 + \frac{m}{m'}\right)^2 \cos^2 kl + \left(m + \frac{1}{m'}\right)^2 \sin^2 kl\right] + \quad \text{(Formula 1)}$$

$$10 \log_{10} \frac{m'}{m}$$

$$m = \frac{S_2}{S_1}, m' = \frac{S_2}{S_3}, k = 2\pi f/c$$

$S_1$=Cross-sectional area of suction port $S_2$=Cross-sectional area of cavity portion
$S_3$=Cross-sectional area of exhaust port TL=Transmitted sound level The present invention is intended to provide a sound muffler in which downsizing is achieved while the function of noise reduction is preserved without using a plurality of sound mufflers by partitioning frequency bands of the noise, or using an expansion-chamber muffler having a large shape.

Means for Solving the Problems

The present inventors have found a sound muffler described below as a solution to such problems. That is, the present invention provides an expansion-chamber muffler, wherein the expansion-chamber muffler is installed in the midway of a tube through which a gas is supplied or evacuated, has an expansion chamber having a larger spatial cross-sectional area than the tube, is equipped with a tube (B) extending from the expansion-chamber muffler on the opposite side of a tube (A) connecting a noise source and the expansion-chamber muffler, and has at least two or more ports for inflow or outflow of a gas on the lateral side of the tube (B).

The present invention also provides the expansion-chamber muffler, characterized in that the end face of the tube (B) is closed.

The present invention also provides the expansion-chamber muffler, characterized in that a plurality of the ports provided on the lateral side of the tube (B) in the longitudinal direction each have different hole diameters, wherein the plurality of the ports provided on the lateral side of the tube (B) in the longitudinal direction are arranged in such a way that the hole diameter increases from the proximity of the expansion chamber.

Further, the present invention provides the expansion-chamber muffler, characterized in that the tube (B) extending from the expansion chamber is bent into a U-shape in the midway.

The present invention also provides the expansion-chamber muffler, which is a suction sound muffler installed on a suction tube of an air compression means for compressing and supplying air.

Further, the present invention provides an oxygen concentration device for providing an oxygen-enriched air by separating air from the atmosphere, comprising:
an adsorption cylinder filled with an adsorbent which preferentially adsorbs nitrogen rather than oxygen;
an air compression means for supplying compressed air to the adsorption cylinder; and an expansion-chamber muffler disposed at a suction port of the air compression means, wherein the expansion-chamber muffler is equipped with an air suction filter having a filter for collecting dust in the air and a case housing the filter, and the tube (B) is a member integrally molded with the case part of the suction filter.

Further the present invention provides the oxygen concentration device equipped with a humidifier for humidifying the oxygen-enriched air, wherein the humidifier which is unified with the filter case utilizes a hollow fiber moisture permeable membrane, wherein air from the atmosphere is supplied to the outside of the hollow fiber, subsequently humidifies the oxygen-enriched air which is fed to the inside of the hollow fiber, and is passed through the filter to serve as the raw material air for the oxygen concentration device.

Advantageous Effects of Invention

Provided by the present invention is a sound muffler as a downsized and weight-reduced sound muffler which preserves a sound reducing function, as well as an oxygen concentration device that uses the sound muffler.

BRIEF DESCRIPTION OF DRAWINGS

FIGS. 1 to 3 show an expansion-chamber muffler as exemplary embodiments of the present invention.

DESCRIPTION OF EMBODIMENTS

An exemplary embodiment of the sound muffler of the present invention will be explained using the drawings. However, the present invention is not intended to be limited to the exemplary embodiment depicted in the drawings. Furthermore, the drawings illustrate a pressure-swing adsorption type oxygen concentration device equipped with a sound muffler as an example, but they are not intended to specify an oxygen concentration method and the method is not limited to any particular oxygen concentration device.

Figure 1:
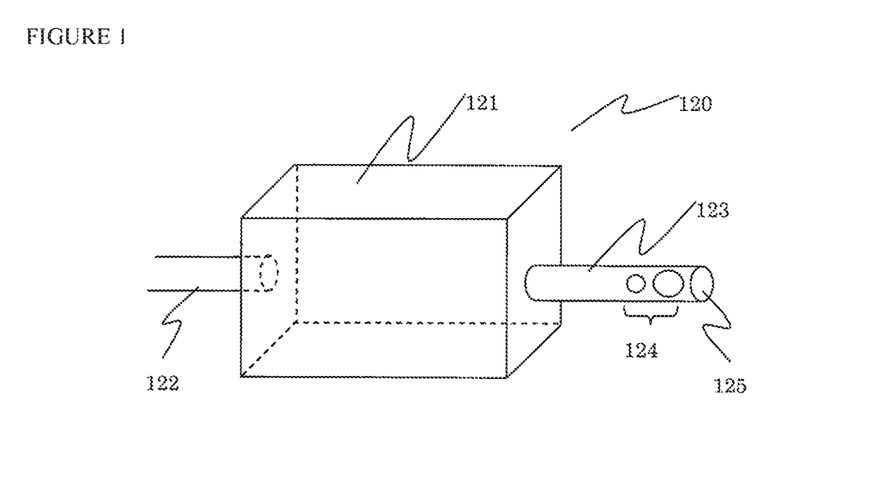
FIG. 1 shows an external view of a sound muffler 120, where the expansion chamber forming the cavity is a cuboid.
Figure 2:
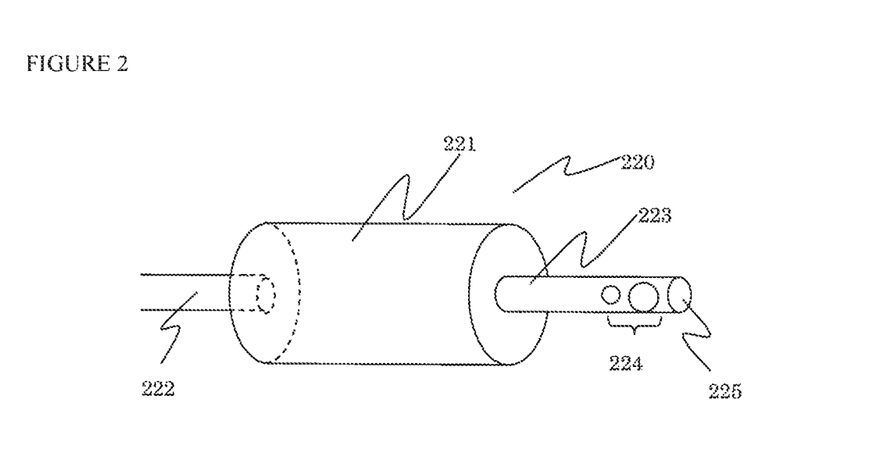
FIG. 2 shows an external view of a sound muffler 220, where the expansion chamber is cylindrical.
Figure 3:
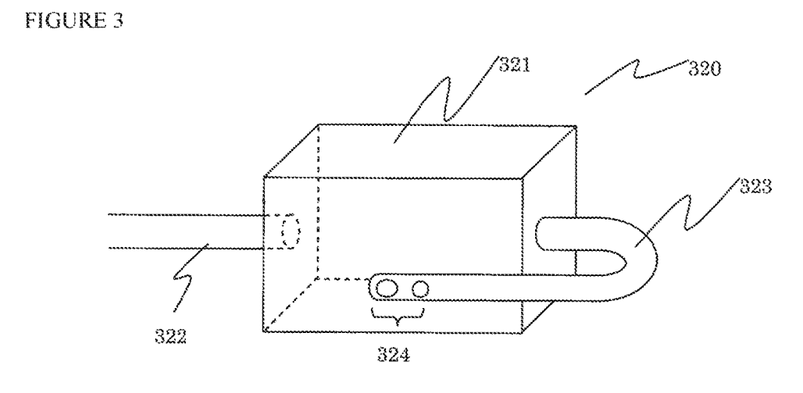
FIG. 3 shows an external view of a sound muffler 320, wherein a tube (B), a tail pipe extending from the cuboid expansion chamber is U-shaped

FIGS. 1 to 3 show a sound muffler as an exemplary embodiment of the present invention. Since these figures do not describe the direction of the airflow flowing inside a sound muffler, the sound muffler can be used as a suction sound muffler or an exhaust sound muffler, and hereafter described is an example of using as a suction sound muffler where tubes (A) (122), (222), and (322) are connected to a compressor at the suction side. FIG. 2 shows a expansion-chamber muffler in which the expansion chamber (221) constituting a cavity is cylindrical. However, it is preferable to adopt the expansion chamber (121) having a rectangular cross section as described in FIG. 1 to reduce the dead space in the housing of the oxygen concentration device. Since the shape of cross section of the expansion chamber of the sound muffler hardly affects the performance in reducing noise, the shape can be selected based on manufacturing cost, manufacturing simplicity and the like.

A conventional sound muffler is generally designed by a theoretical formula shown as Formula 1 above. However, since Formula 1 is a theoretical formula that does not consider the reflectivity of the sound, there are cases where the noise in the low frequency range is not sufficiently attenuated in the sound muffler designed by Formula 1, and in such cases the problem has been dealt with by increasing the length or the cross-sectional area of the cavity unit of the expansion chamber.

As a method alternative to this, it is well known that the performance close to the theoretical value can be obtained by forming a structure provided with a tube (B) (123, 223) generally called a tail pipe. Obtaining the sound reducing effect by the tube (B) (123, 223) requires a sufficient length of the tube (B), however the dead space in the device is increased by securing a sufficient length for the sufficient sound reducing effect. Therefore, the length of the tail pipe needs to be shortened when adopted in a sound muffler in practice, and in order to eliminate the dead space in the device, the method of increasing the cavity of the expansion chamber has been selected in many devices instead of adopting the structure having the tail pipe with the predetermined length.

In the present invention, as a result of intensive studies, as shown in FIG. 3, provided is a structure which prevents the dead space from being increased and maintains a sufficient length of the tube (B) (323) by shaping the tube (B) (323), which is a tail pipe, into a U-shaped form and minimizing the portion protruding from the expansion chamber (321). By having such structure, the length of the tube (B) (323) can be extended to about the same length of the cavity of the expansion chamber (321). Further, the dead space can be reduced by placing the linear portion of the tube B (323) beyond the U-shaped part in such a way as to make a close contact with the expansion chamber (321).

Figure 4:
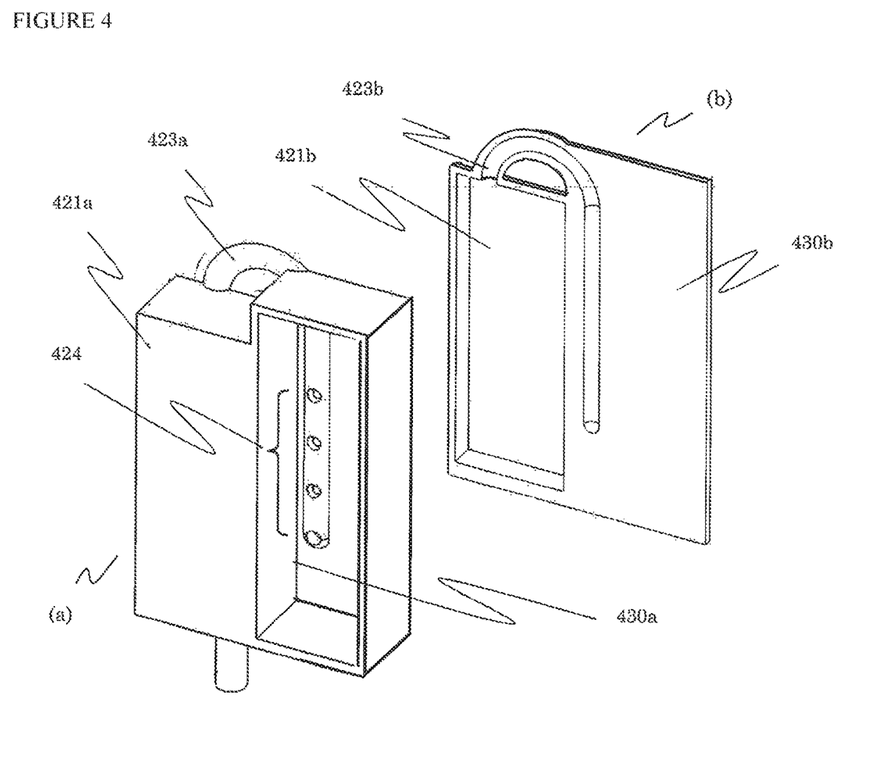
FIG. 4 shows a structural view of a sound muffler where an expansion-chamber muffler, another exemplary embodiment of the present invention, is integrally molded with a filter case.

Furthermore, as shown in FIG. 4, the dead space can be eliminated except for the portion of the U-shaped pipe by integrally structuring the filter case (430*a*) of the air suction filter and the bottom portion of the filter case (430*b*), that are components of the oxygen concentration device, with the tube (B) (423).

In the present invention, as shown in FIGS. 1 and 2, the suction port (124, 224) of the sound muffler is provided on the lateral side of the tube B (123, 223). In general, the suction port is often provided on the end face (125, 225, 325) of the tube (B) when extending the tube (B) (123, 223, 323) in a straight line, where such site becomes the source of the suction sound. As shown in FIG. 4 in particular, in the sound muffler having a structure where two separate constructional members of the sound muffler are injection-molded and both members are later joined by ultrasonic welding or hot plate welding, a new airflow noise may occur from the end face of the tube (B) (423). Since the frequency of this noise is in the high frequency band, it is possible to attenuate and eliminate the noise by the structure surrounding the sound muffler, however it is preferable not to generate the noise if possible.

Therefore, in the present invention, as shown in FIGS. 1-3, the end face (125, 225, 325) of the tube (B) is closed and at least two or more suction ports (124, 224, 324) are provided on the lateral side of the tube (B) (123, 223, 323). This is because a new airflow noise is increased at the suction site by having only one suction port, and having a plurality of two or more suction ports (124, 224, 324) reduces the airflow noise generated in each suction port, thus making it possible to reduce the noise as a whole. In addition, by making the size of the suction port (124, 224, 324) smaller at a position closer to the cavity of the expansion chamber (12, 221, 321) and larger at a position of the end face of the tube (B) (123, 223, 323), the occurrence of airflow noise can be suppressed more efficiently and the pressure loss occurring at such place is effectively reduced.

An expansion-chamber muffler as shown in FIG. 4, as another exemplary embodiment of the present invention, is unified with a filter case formed by bonding two separate resin molded members (a) and (b) together. FIG. 4 shows an external view of a molded article divided at the expansion chamber (421) of the expansion-chamber muffler and the portion of the tube (B) (423) which is a suction pipe, wherein the expansion-chamber muffler is produced by bonding two parts by ultrasonic welding. As described above, the structure is made in such a way that multiple suction ports (424) are incorporated inside the filter case portion (430*a*). This allows effective use of the previously described dead space and makes it possible to obtain the effect of the sound insulation by the filter mounted in the filter case part against the airflow noise generated at the suction ports (424), thus enabling a further noise reduction.

Figure 9:
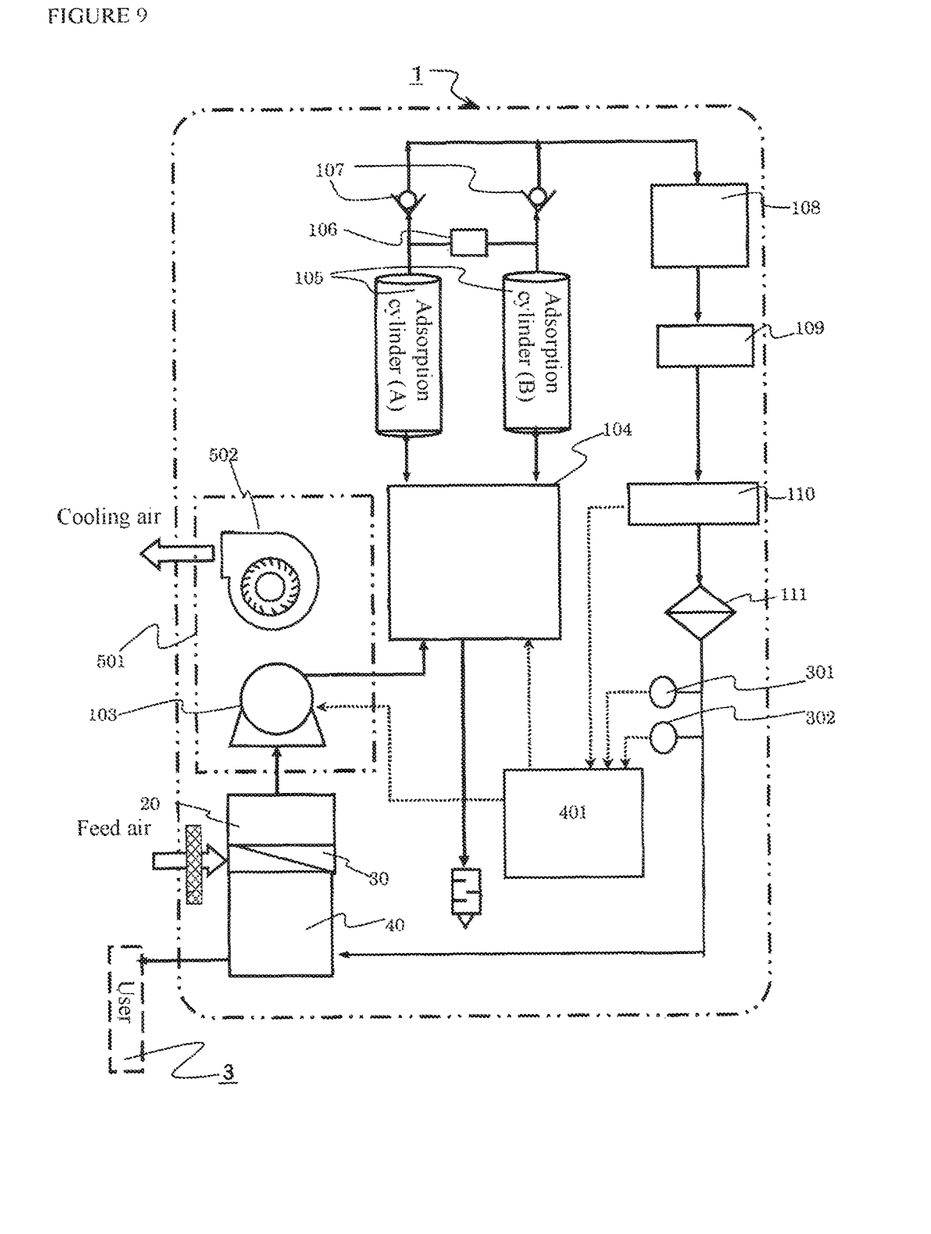
FIG. 9 shows a structural view of an oxygen concentration device utilizing the sound muffler of the present invention.

FIG. 9 shows a schematic structural view of a device illustrating a pressure-swing adsorption type oxygen concentration device as an exemplary embodiment of the present invention. In FIG. 9, (1) indicates an oxygen concentration device and (3) indicates the user (patient) who inhales the oxygen-enriched air that has been humidified. The pressure-swing adsorption type oxygen concentration device (1) is equipped with an external air suction filter (30), a suction sound muffler (20), a compressor (103), flow path switching valves (104) and (106), an adsorption cylinder (105), a check valve (107), a product tank (108), a pressure regulating valve (109), a flow rate setting means (110), and a particle filter (111). This makes it possible to produce the oxygen-enriched air by concentrating oxygen from the feed air taken from the outside. Further, incorporated inside the housing of the oxygen concentration device are a humidifier (40) for humidifying the produced oxygen-enriched air, a control means (401) for controlling the compressor (103) and the flow path switching valves (104) and (106) by using a set value of the flow rate setting means (110) and measured values of an oxygen concentration sensor (301) and a flow-rate sensor (302), a compressor box (501) for suppressing the noise of the compressor, and a cooling fan (502) for cooling the compressor.

Figure 5:
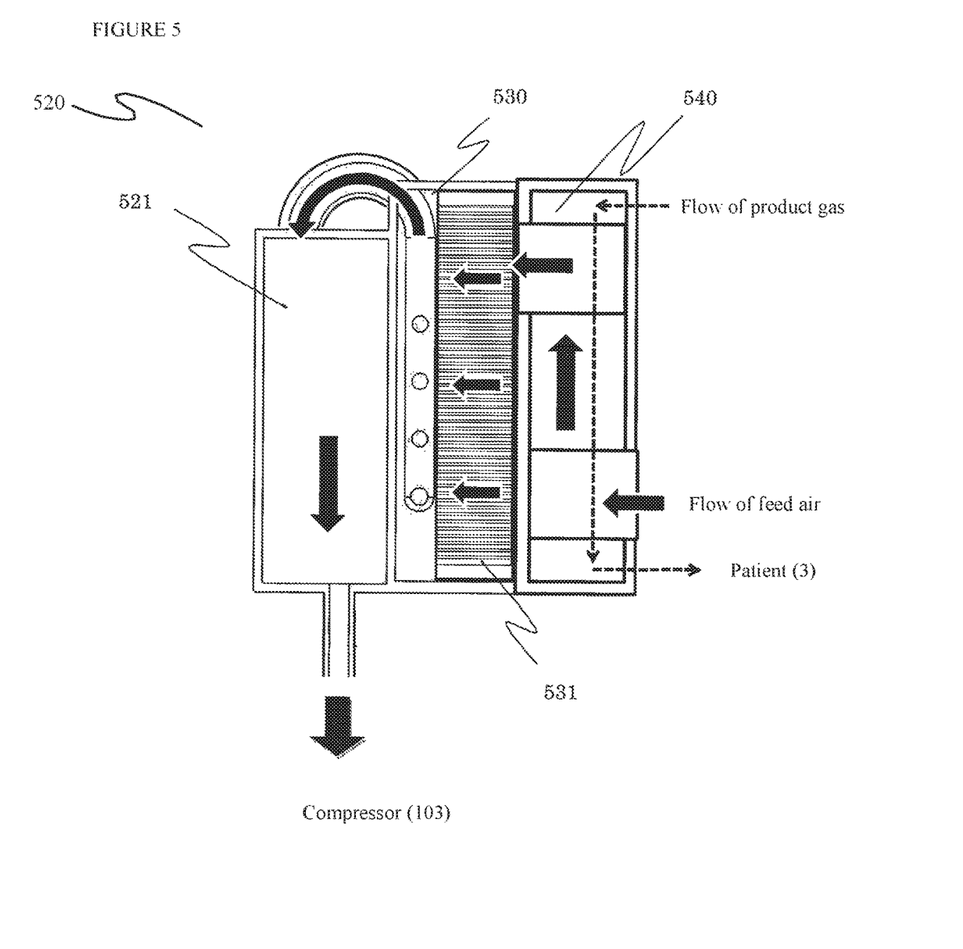
FIG. 5 shows a structural view of a sound muffler where an expansion-chamber muffler 521, another exemplary embodiment of the present invention, is unified with a filter unit 531 and a humidifier 540.

In another exemplary embodiment of a expansion-chamber muffler in the present invention, as shown in FIG. 5, a suction sound muffler (520) is unified not only with an external air suction filter (530), but also with a humidifier (540) which uses a water permeable hollow fiber membrane. Such humidifier transmits the moisture in the atmosphere to the product gas using a difference in the water vapor partial pressure and moderately humidifies the oxygen-enriched air having practically zero relative humidity through a water permeable hollow fiber membrane bundle such as polyimide, wherein the oxygen-enriched air which is the product gas is flowed into the primary side (inside) of the hollow fiber, and the air for the humidification purpose is flowed into the secondary side (outside) of the hollow fibers. Further, since the feed air on the secondary side which has passed through the humidifier is dried by the amount of water given to the product gas, it can contribute to the extension of life of the humidity-sensitive adsorbent in the pressure-swing type adsorption system. In a conventional humidifier which uses the water permeable hollow fiber, the air on the secondary side is forcefully flowed by an axial flow fan, a centrifugal fan or the like in order to efficiently humidify the product gas on the primary side. In the present invention, however, since the flow on the secondary side is substituted with the flow of the feed air, mounting of a fan became unnecessary, and reduction in size, weight and cost, as well as elimination of the fan noise were achieved. In addition, by integrating the humidifier at the upstream side of the filter, it becomes possible to attenuate the noise transmitted through the expansion-chamber muffler and the filter further in the housing portion of the humidifier.

EXAMPLES

The reduction effect of the compressor noise by the expansion-chamber muffler of the present invention is shown below. In an anechoic chamber, the expansion-chamber muffler of the present invention was connected to the compressor at the feed air supply side and the reduction effect was confirmed on the noise leaking from the suction side.

Figure 6:
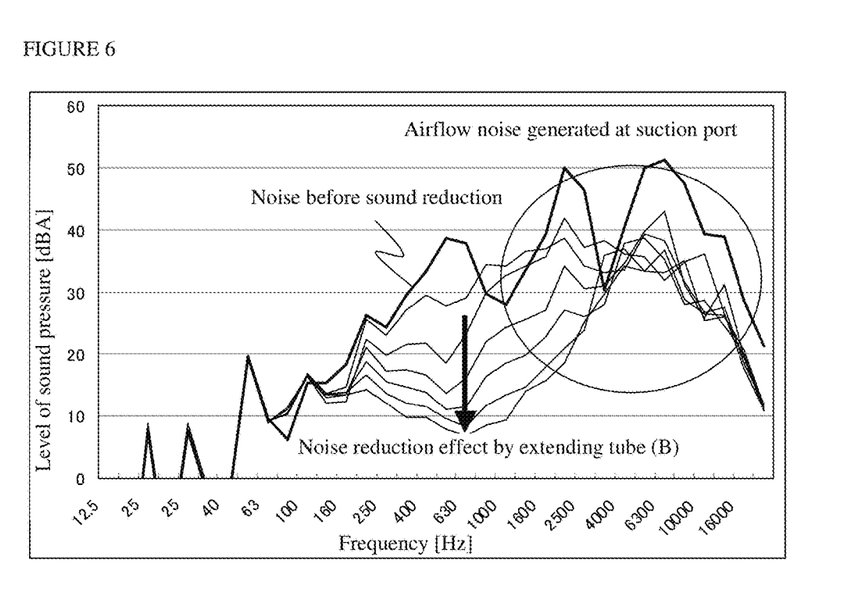
FIG. 6 shows the sound reducing effect in the low frequency band by the sound muffler of the present invention where the length of the tube (B) is extended.

FIG. 6 shows the noise reduction effect by the tube (B), which is one of the features of the present invention. The expansion-chamber muffler shown in FIG. 1 having two suction ports (124) with the hole diameter of 6 mm on the lateral side of the tube (B) (123) is used. This is a good example demonstrating that the noise reduction effect is observed in the low frequency band of 800 Hz or less by progressively increasing the length of the tube (B) (123). As such, the noise reduction effect in the low frequency band is obtained just by extending the length of the tube (B) (123) without extending the cavity length or increasing the spatial cross-sectional area. However, the noise reducing effect in the high frequency band of 1000 Hz or more is insignificant, and in some cases, even a larger airflow noise may be generated after mounting the sound muffler.

Figure 7:
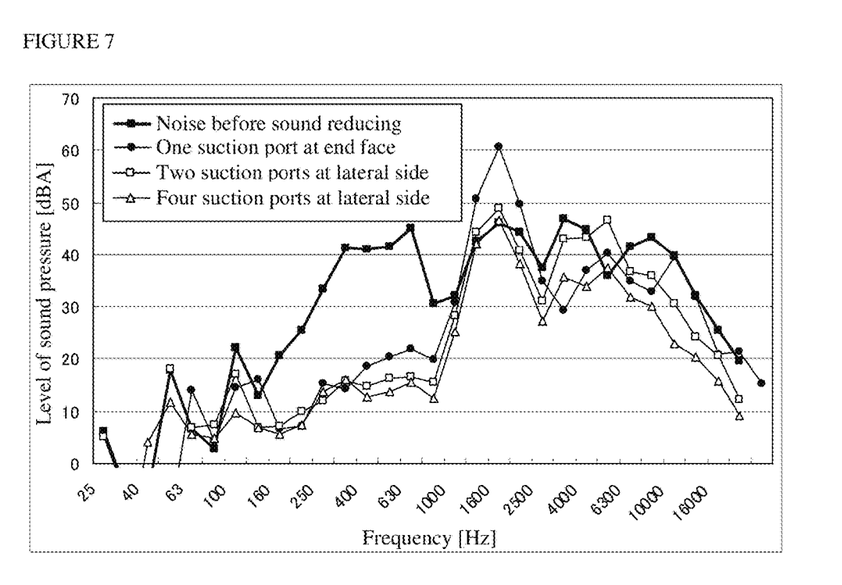
FIG. 7 shows the sound reducing effect in the high frequency band by the sound muffler equipped with the tube (B) of the present invention having suction ports on its lateral side.

FIG. 7 shows a comparison of noise reducing effect among the expansion-chamber muffler described in FIG. 1, where two suction ports (124) with a hole diameter of 6 mm are provided on the lateral side of the tube (B) (123) and the end face (125) is closed (indicated by □ in Figure), the sound muffler having four suction ports (indicated by Δ in Figure), and the sound muffler in which one suction port is provided on the end face of the tube (B) (hereinafter referred to as a conventional sound muffler) (indicated by closed circles in Figure). The length of the tube (B) is the same in all sound mufflers and the length of those which showed the highest noise reducing effect in FIG. 6 is used. It is found that the sound muffler of the present invention equipped with two or more suction ports on the lateral side of the tube (B), unlike the conventional sound muffler, does not generate a new airflow noise in the high frequency band of 1000 Hz or more and has in part a noise reducing effect.

Figure 8:
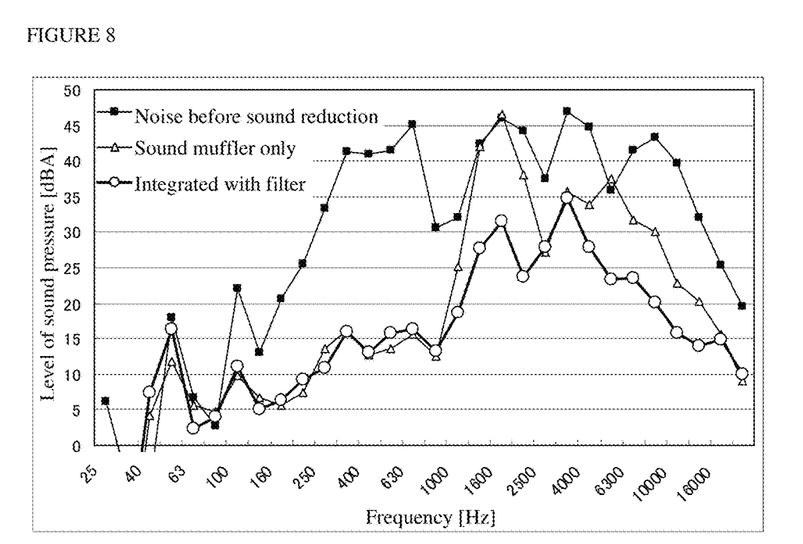
FIG. 8 shows the sound reducing effect of the sound muffler where the sound muffler of the present invention is unified with a filter unit.

Furthermore, FIG. 8 shows the noise reducing effect of the sound muffler of the present invention shown in FIG. 4. It is clearly shown that, by integrating the sound muffler of the present invention with the filter unit, the noise reducing effect by the expansion-chamber muffler as well as the sound absorption effect by the filter can be achieved and the significant noise reducing effect is obtained in noises in the high frequency band such as those that cannot be attenuated by the sound muffler or a newly generated airflow noise.

INDUSTRIAL APPLICABILITY

The oxygen concentration device of the present invention, as a medical oxygen concentration device, is used as an oxygen supply source in an oxygen inhalation therapy for patients suffering from respiratory disease such as asthma, pulmonary emphysema, chronic bronchitis, and the like. The oxygen concentration device can be further used as a down-sized and weight-reduced oxygen concentration device while keeping the noise reduction function by adopting the sound muffler which is a feature of the present invention.

The invention claimed is:

1. An expansion-chamber muffler, which is a suction sound muffler, installed in a suction tube of an air compression means for compressing and supplying air and provided with an expansion chamber having a spatial cross-sectional area larger than that of the tube, the muffler comprising:
   a tube (B) extending from the expansion-chamber muffler on the opposite side of a tube (A) connecting a noise source and the expansion-chamber muffler; and
   at least two ports for inflow or outflow of a gas on a lateral side of the tube (B) relative to a longitudinal direction of the tube (B),
   wherein the at least two ports provided on the lateral side of the tube (B) each have different hole diameters, and
   wherein the at least two ports are arranged in such a way that the hole diameter of the ports increase sequentially as the distance from the expansion chamber increases.

2. The expansion-chamber muffler according to claim 1, wherein an end face of the tube (B) is closed.

3. The expansion-chamber muffler according to claim 1, wherein the tube (B) extending from the expansion chamber is bent into a U shape in the midway.

4. The expansion-chamber muffler according to claim 1, wherein the expansion-chamber muffler is equipped with a suction filter having a filter for collecting dust in the air and a case for housing the filter, wherein the tube (B) is a member integrally molded with the case part of the suction filter.

5. An oxygen concentration device for supplying an oxygen-enriched air by separating oxygen from atmospheric air, comprising:
- an expansion-chamber muffler that includes a suction filter for collecting dust in the atmospheric air and a humidifier for humidifying oxygen-enriched air,
- wherein a tube (A) extends from an expansion chamber of the expansion-chamber muffler and connects a noise source to the expansion chamber, and
- wherein a tube (B) extends from the expansion chamber, a filter case for housing the suction filter is integrally molded with the tube (B) and unified with the humidifier.

6. An oxygen concentration device for supplying an oxygen-enriched air by separating oxygen from the air, comprising an adsorption cylinder filled with an adsorbent which preferentially adsorbs nitrogen rather than oxygen and an air compression means for supplying compressed air to the adsorption cylinder, wherein the expansion-chamber muffler according to claim 4 provided at the suction port of the air compression means.

7. The oxygen concentration device according to claim 5, wherein a plurality of ports provided on a lateral side of the tube (B) each have different hole diameters, wherein the at least two ports are arranged in such a way that the hole diameters of the ports increase sequentially as the distance from the expansion chamber increases.

8. The oxygen concentration device according to claim 5, further comprising:
- an air compression means for supplying compressed air to an adsorption cylinder, the expansion-chamber muffler is installed on a suction tube of the air compression means.

9. The oxygen concentration device according to claim 8, wherein the adsorption cylinder is filled with an adsorbent, the adsorbent preferentially adsorbs nitrogen rather than oxygen.

10. The oxygen concentration device according to claim 7, wherein at least two or more ports for inflow or outflow of a gas are on the lateral side of the tube (B) relative to a longitudinal direction of the tube (B).

11. The oxygen concentration device according to claim 10, wherein the ports each have different hole diameters.

12. The oxygen concentration device according to claim 10, wherein the ports are arranged in such a way that hole diameters of the ports increase sequentially as a distance from the expansion chamber increases.

13. The oxygen concentration device according to claim 5, wherein the humidifier is comprises a hollow fiber moisture permeable membrane.

14. The oxygen concentration device according to claim 13, wherein the atmospheric air that is supplied to the hollow fiber moisture permeable membrane humidifies the oxygen-enriched air.

15. The oxygen concentration device according to claim 13, wherein the oxygen-enriched air is fed to the inside of the hollow fiber moisture permeable membrane and passes through the suction filter to serve as raw material air for the oxygen concentration device.

16. The oxygen concentration device according to claim 5, wherein the expansion chamber is between the tube (A) and the tube (B).

17. The oxygen concentration device according to claim 5, wherein the tube (B) extends from a side of the expansion chamber that is opposite to the tube (A).

18. The oxygen concentration device according to claim 5, wherein the expansion-chamber muffler has a spatial cross-sectional area larger than that of the tube (A).

19. The oxygen concentration device according to claim 5, wherein the expansion-chamber muffler has a spatial cross-sectional area larger than that of the tube (B).

* * * * *